(12) United States Patent
Keisic

(10) Patent No.: US 8,684,981 B2
(45) Date of Patent: Apr. 1, 2014

(54) URINARY BAG SYSTEM

(75) Inventor: Hollis S. Keisic, Lockport, NY (US)

(73) Assignee: Clinical Comfort Solutions, LLC ( * ) Notice: Subject to any disclaimer, the term of this patent is extended or adjusted under 35 U.S.C. 154(b) by 29 days.

(21) Appl. No.: 13/039,358

(22) Filed: Mar. 3, 2011

(65) Prior Publication Data

US 2011/0224636 A1 Sep. 15, 2011

Related U.S. Application Data

(60) Provisional application No. 61/313,834, filed on Mar. 15, 2010.

(51) Int. Cl.
*A61M 1/00* (2006.01)

(52) U.S. Cl.
USPC ............................................. 604/327; 2/311

(58) Field of Classification Search
USPC .............. 604/328, 353, 317, 327, 580; 2/217, 2/311–315, 317–319, 323, 329; 482/105
See application file for complete search history.

(56) References Cited

U.S. PATENT DOCUMENTS

| | | | | | |
|---|---|---|---|---|---|
| 3,751,031 | A | * | 8/1973 | Yamauchi | 482/105 |
| 4,874,387 | A | * | 10/1989 | Boone | 604/326 |
| 6,461,319 | B1 | * | 10/2002 | Ekey | 602/62 |
| 6,887,223 | B2 | * | 5/2005 | Bisbee | 604/353 |
| 2006/0293631 | A1 | * | 12/2006 | Bolt | 604/353 |

* cited by examiner

*Primary Examiner* — Melanie Hand
(74) *Attorney, Agent, or Firm* — Jennifer Meredith, Esq.

(57) ABSTRACT

A urinary bag system comprising: a substantially tubular leg portion having at least one support opening along a top portion; a substantially rectangular urine bag pouch affixed to the substantially tubular leg portion, having a top side, left side, right side, bottom side, outside side portion, inside side portion, and a substantially rectangular cutout opening along the outside side portion and corresponding inside side portion of the substantially rectangular urine bag pouch, a valve opening along the bottom side and a top opening along the top side; a support garment; at least one strap having at least one attachment device, a first end and a second end, the first end removably attached to the support garment by at least one attachment device and the second end removably attached to at least one support opening along a top portion of the substantially tubular leg portion by at least one attachment device.

17 Claims, 37 Drawing Sheets

URINARY BAG SYSTEM

This application claims priority to provisional patent application No. 61/313,834, filed Mar. 15, 2010 and entitled "The Brody Belt" the entire contents of which are incorporated herein by reference.

BACKGROUND OF THE INVENTION

Field of the Invention

The present invention relates generally to a urinary bag holder system and methods of using the system that secure a patient's urinary drainage bag providing the user with increased mobility, comfort and ease of use.

Urine Leg bags are frequently used by patients suffering from urinary incontinence, or during recovery from surgery. The leg bags are typically equipped with inlet and outlet tubes and are designed to be strapped to the patient's leg and receive urine from a catheter or collection tube. It is important that the bag be comfortable and reduce contact with the patients leg, particularly during any movement. The bag holder system should allow the urine bag to be easily attached, detached, leak proof in use and comfortable to wear.

Urine bag holding devices of the past typically utilize numerous straps wrapped around the leg of the user, to attach the urine bag to the leg of the user. An example is disclosed in U.S. Pat. No. 4,421,509. Because of the weight of the bag, particularly when filled with urine, the device can slide down the leg of the user.

Prior art bags often tend to buckle in use, increasing the chances of kinking, obstruction, backflow, disconnection and even possible rupture of the bag. Also, buckling can create pressure points that dig into the user's leg. Finally, the nozzles, clamps and valves can make contact with the skin on the wearer during normal use causing discomfort to the user and even sores or ulcers.

The present invention seeks to overcome all of these issues, providing a urinary bag system that is easy to use, comfortable, does not buckle in use and avoids making contact with the skin of the wearer.

SUMMARY OF THE INVENTION

The present invention relates to urine bag holding devices, systems and methods.

According to one aspect of the present invention, a urinary bag system is provided comprising: a substantially tubular leg portion having at least one support opening along a top portion; a substantially rectangular urine bag pouch affixed to the substantially tubular leg portion, the substantially rectangular urine bag pouch having a top side, left side, right side, bottom side, outside side portion and inside side portion, and having a substantially rectangular cutout opening along the outside side portion and corresponding inside side portion of the substantially rectangular urine bag pouch, a valve opening along at least a portion of the bottom side and a top opening along the top side; a support garment; at least one strap having at least one attachment device, a first end and a second end, the first end removably attached to the support garment by the at least one attachment device and the second end removably attached to the at least one support opening along a top portion of the substantially tubular leg portion by at least one attachment device.

According to another aspect of the present invention, a urinary bag system is provided comprising: a substantially tubular leg portion having at least one support opening along a top portion; a substantially rectangular urine bag pouch affixed to the substantially tubular leg portion, the substantially rectangular urine bag pouch having a top side, left side, right side, bottom side, outside side portion and inside side portion, and having a substantially rectangular cutout opening along the outside side portion and corresponding inside side portion of the substantially rectangular urine bag pouch, a valve opening along at least a portion of the bottom side and a top opening along the top side; a gusset between at least a portion of the left side, the right side, the bottom side and the substantially tubular leg portion; a support garment; at least one strap having at least one attachment device, a first end and a second end, the first end removably attached to the support garment by at least one attachment device and the second end removably attached to at least one support opening along a top portion of the substantially tubular leg portion by at least one attachment device.

These and other features, aspects and advantages of the present invention will become better understood with reference to the following description and claims.

DETAILED DESCRIPTION OF THE INVENTION

Figure 1A:
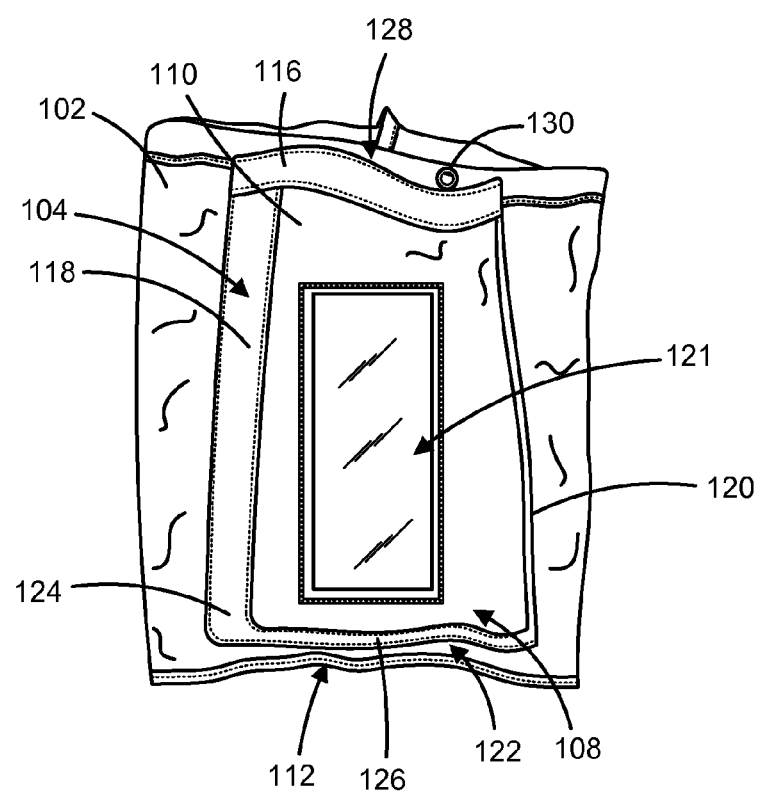
FIGS. 1A-1D depicts a substantially tubular leg portion, according to aspects of the present invention.
Figure 1B:
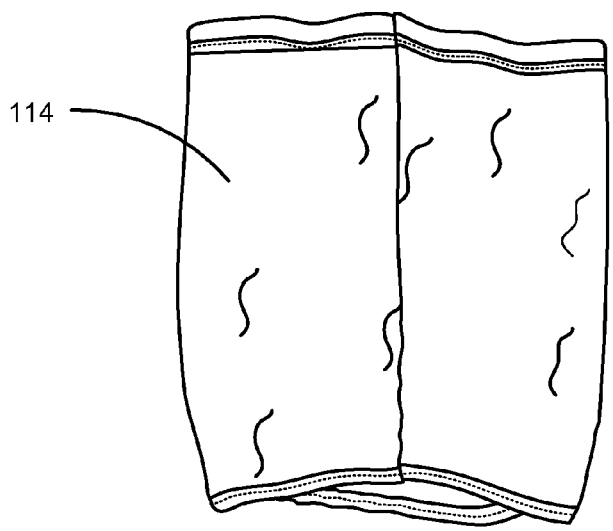
Figure 1C:
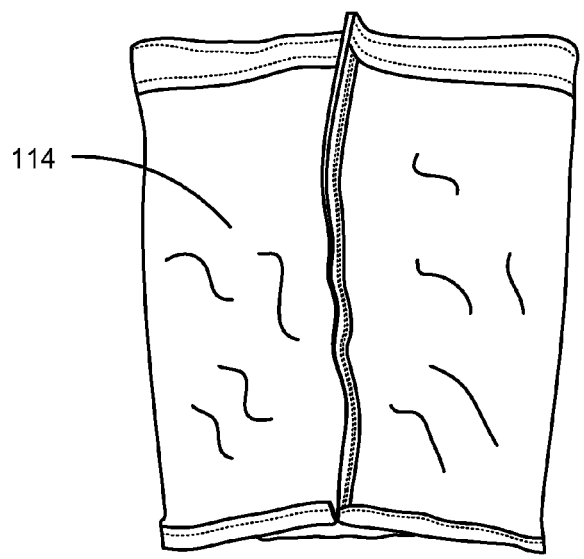
Figure 1D:
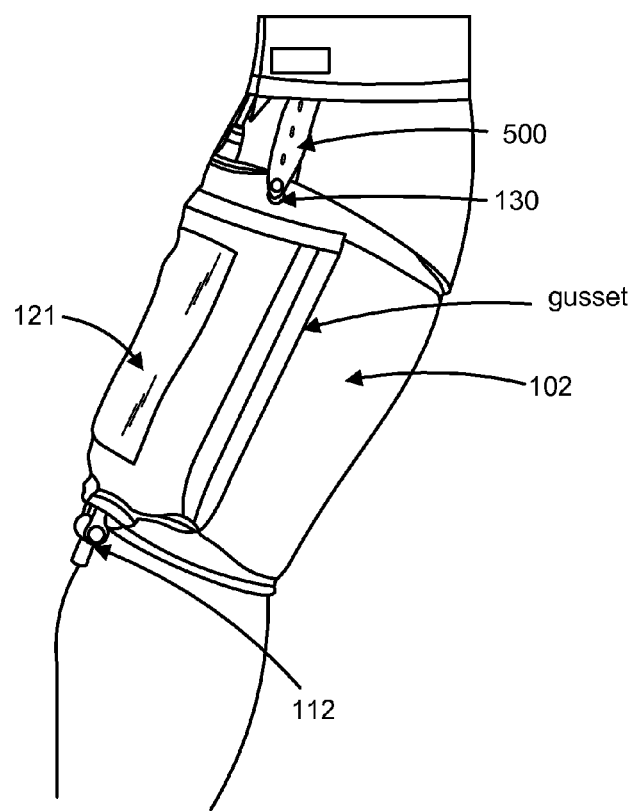
Figure 2A:
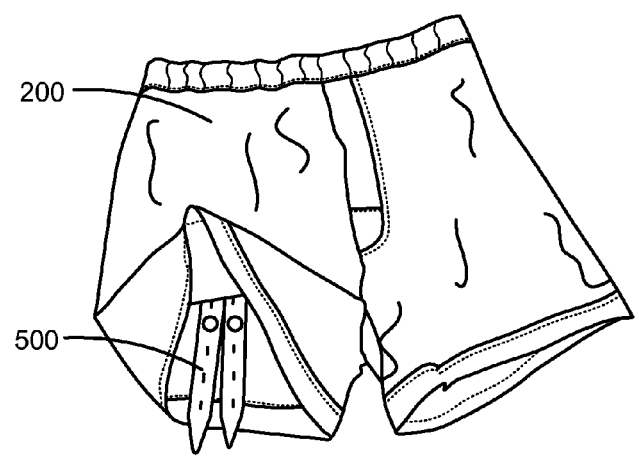
FIGS. 2A-2F depict a urine bag holder system, according to aspects of the present invention.
Figure 2B:
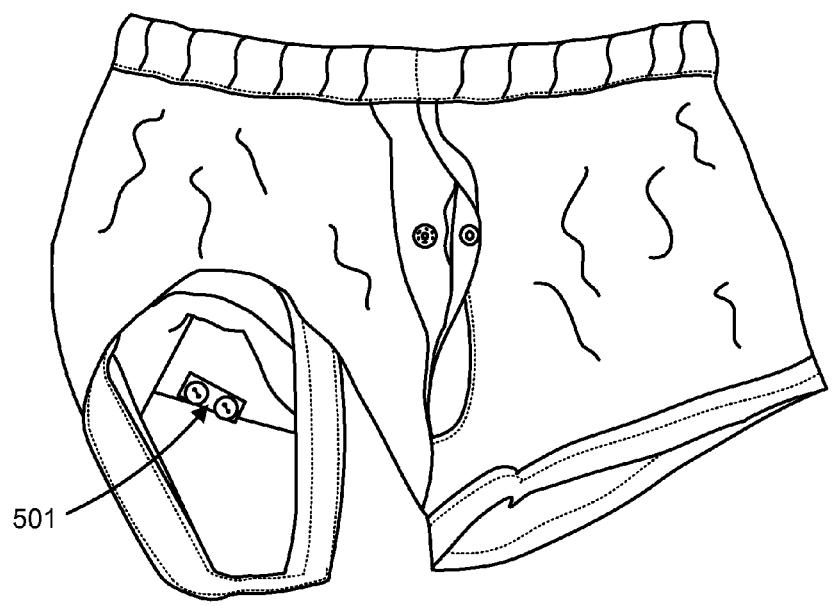
Figure 2C:
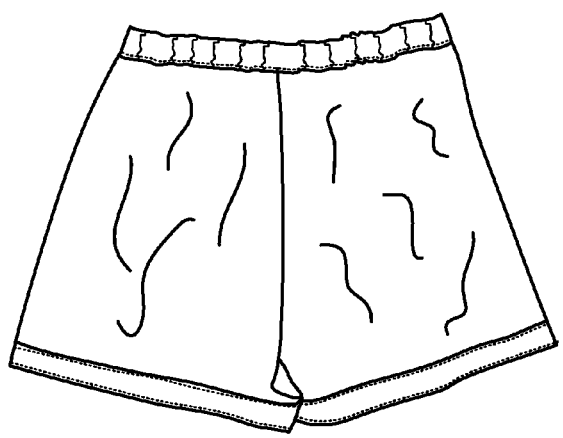
Figure 2D:
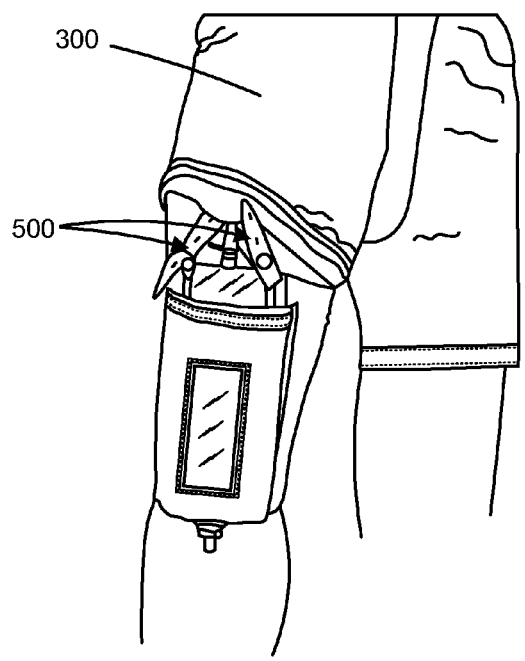
Figure 2E:
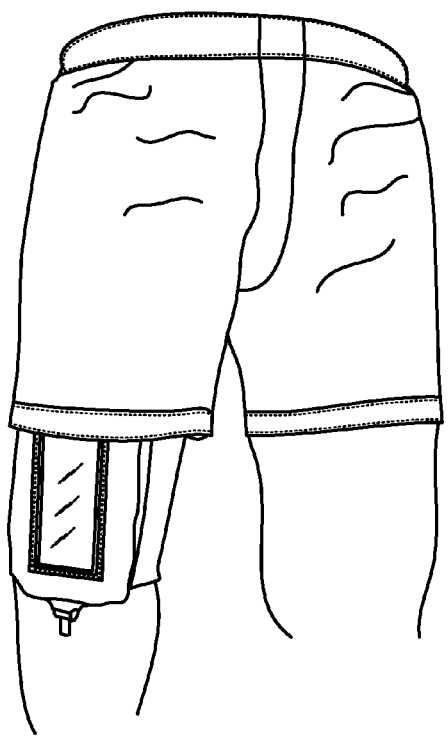
Figure 2F:
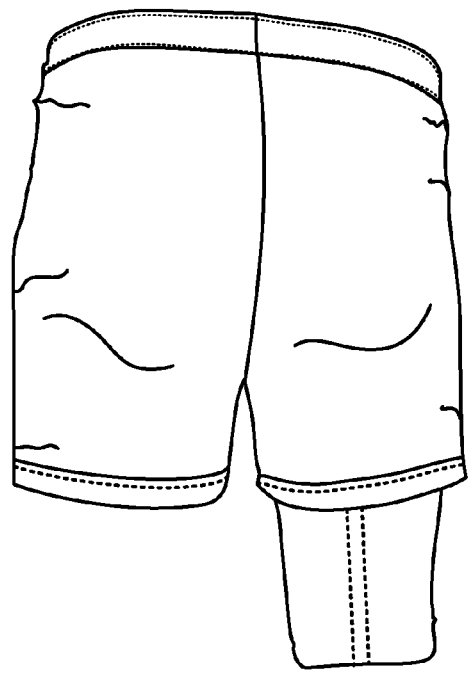
Figure 3A:
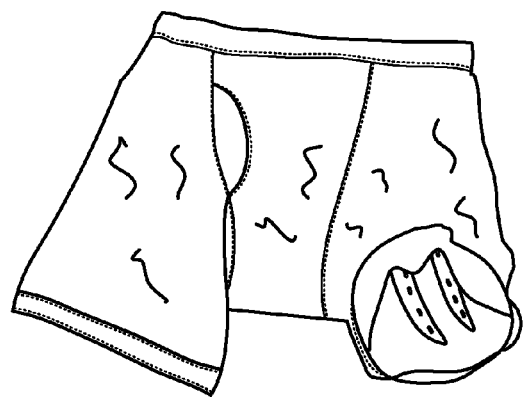
FIGS. 3A-3F depict a urine bag holder system, according to aspects of the present invention.
Figure 3B:
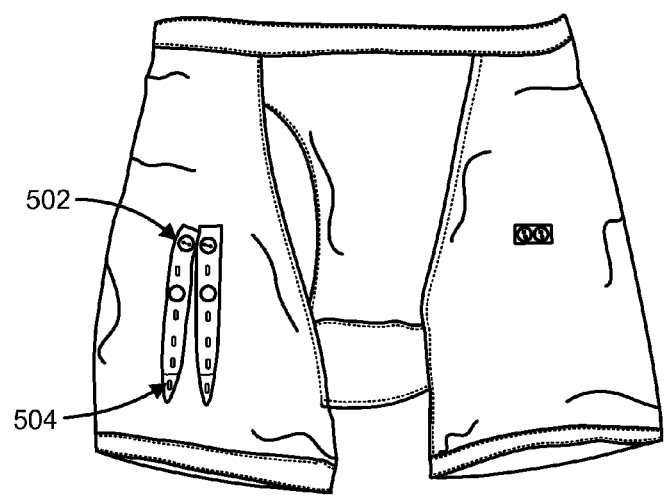
Figure 3C:
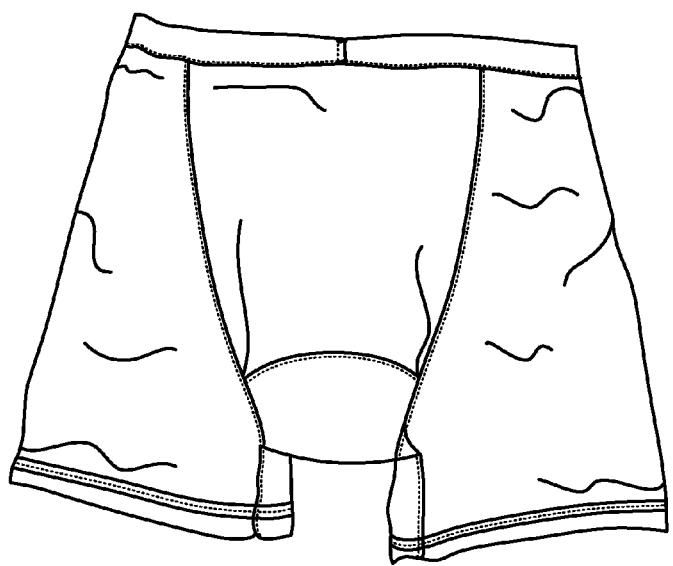
Figure 3D:
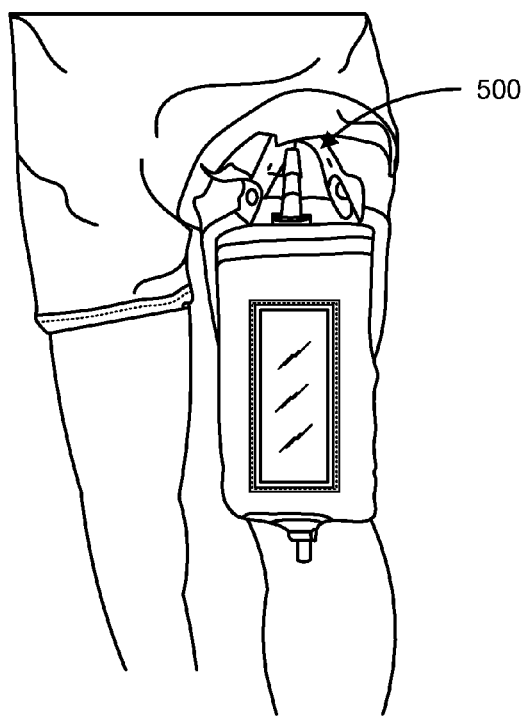
Figure 3E:
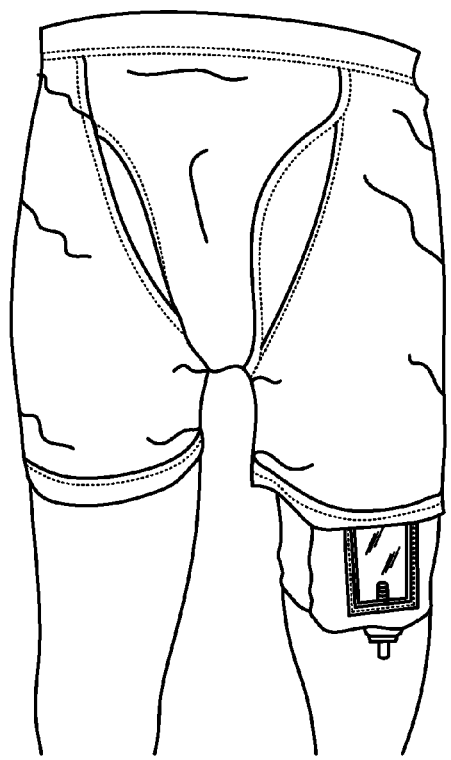
Figure 3F:
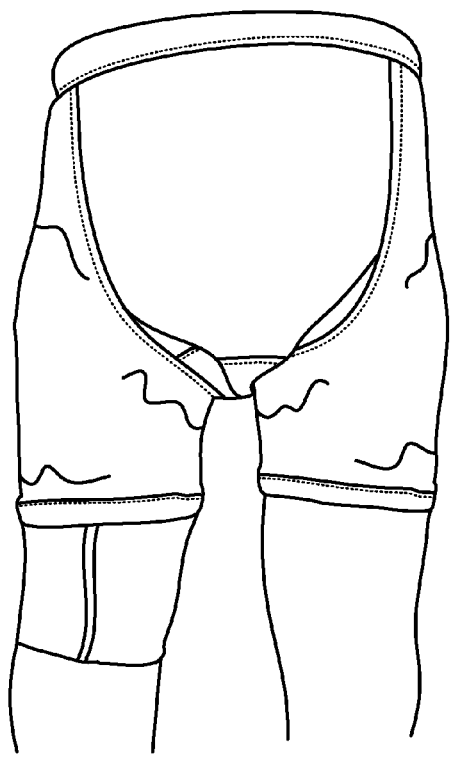
Figure 4A:
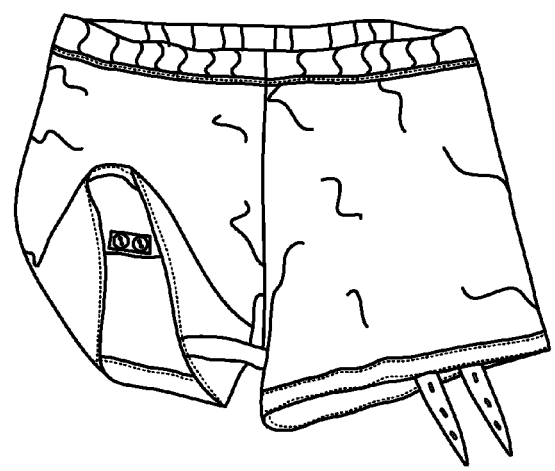
FIGS. 4A-4F depict a urine bag holder system, according to aspects of the present invention.
Figure 4B:
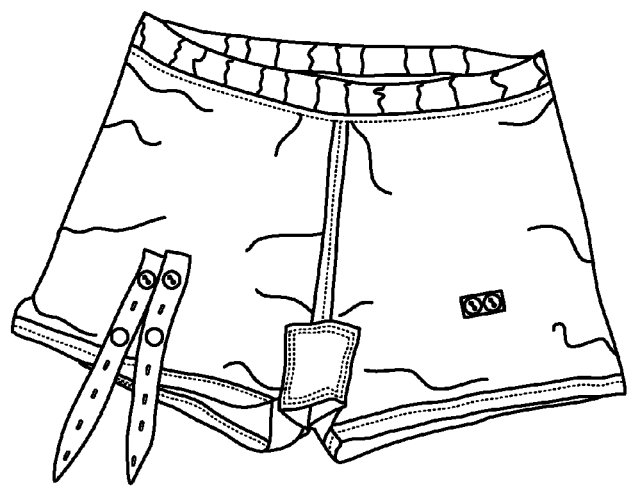
Figure 4C:
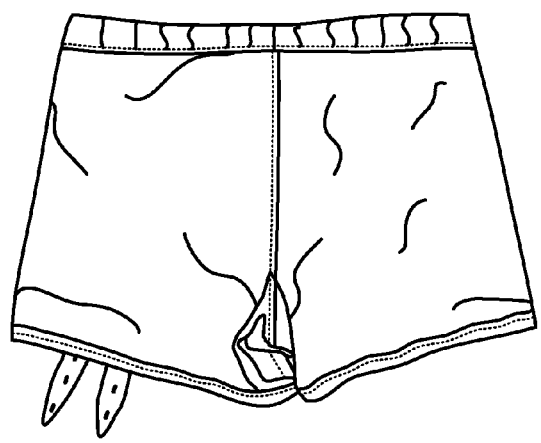
Figure 4D:
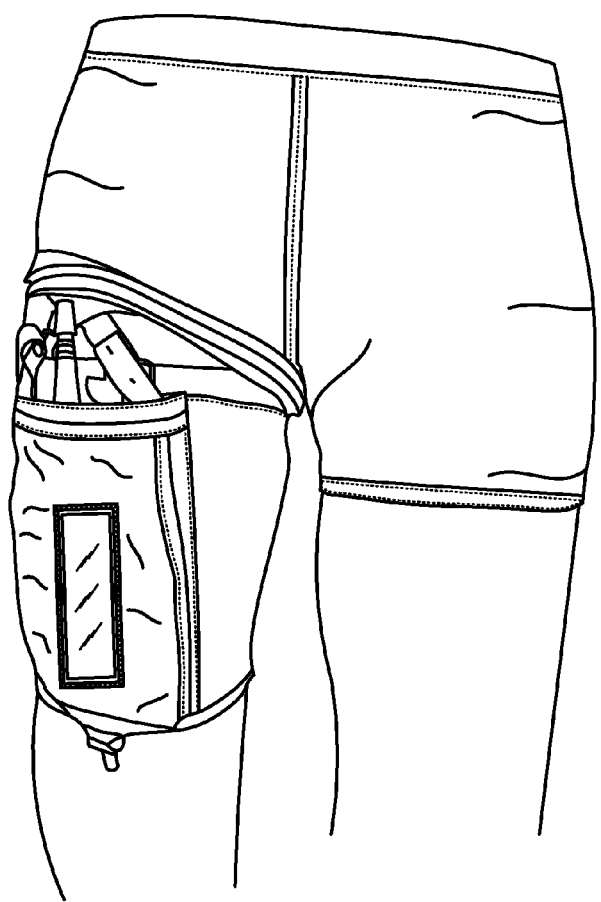
Figure 4E:
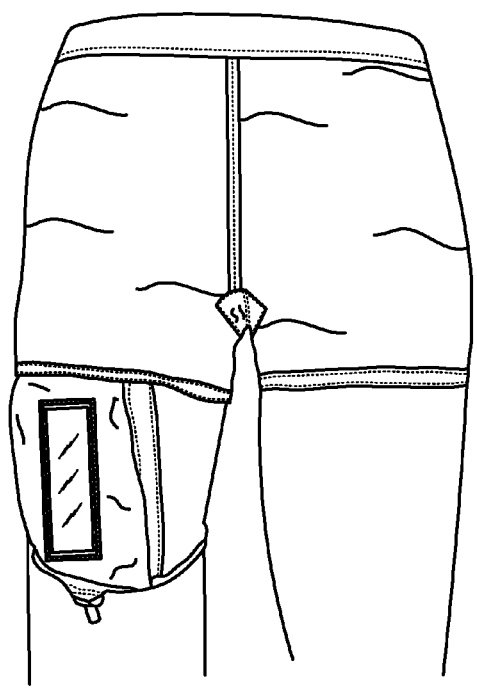
Figure 4F:
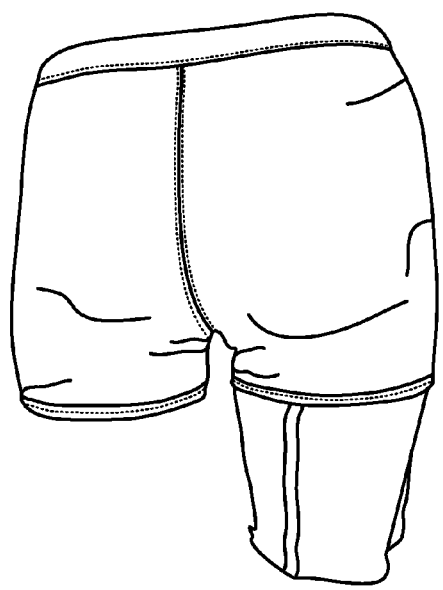
Figure 5A:
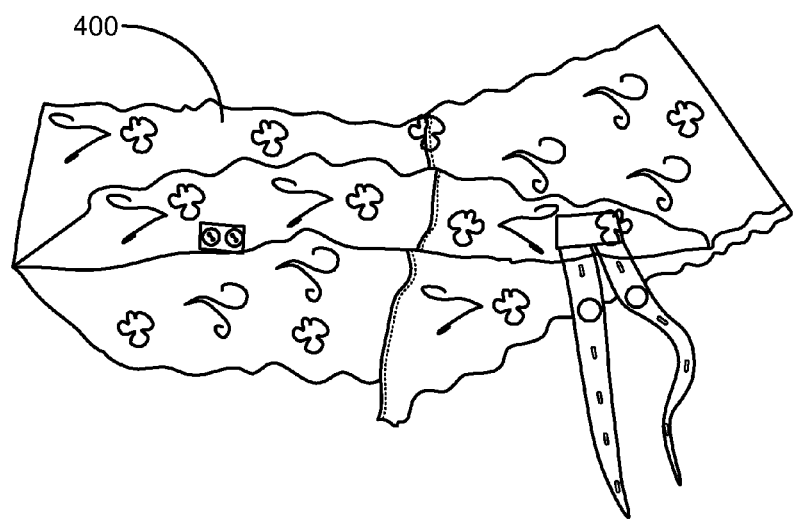
FIGS. 5A-5E depict a urine bag holder system, according to aspects of the present invention.
Figure 5B:
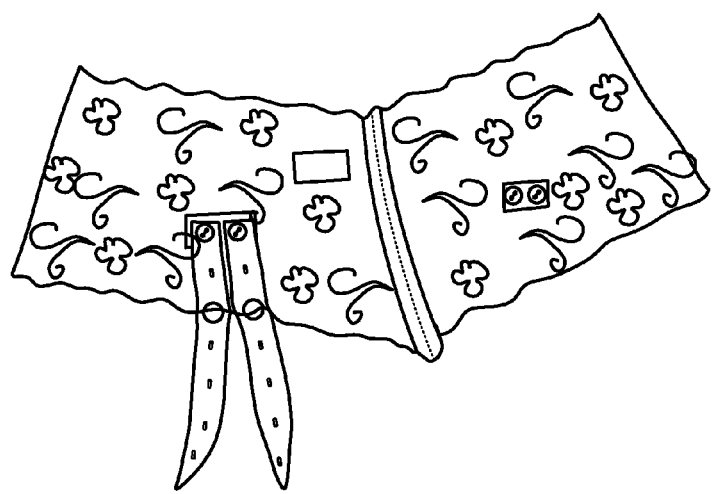
Figure 5C:
Figure 5D:
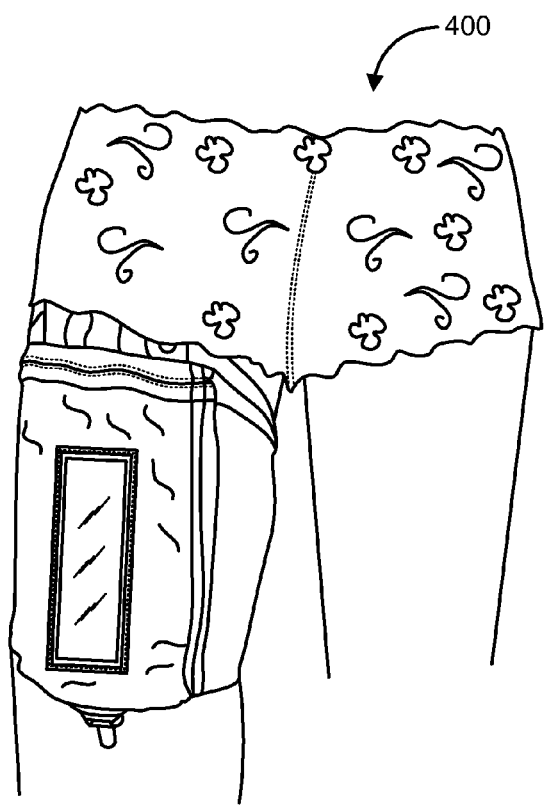
Figure 5E:
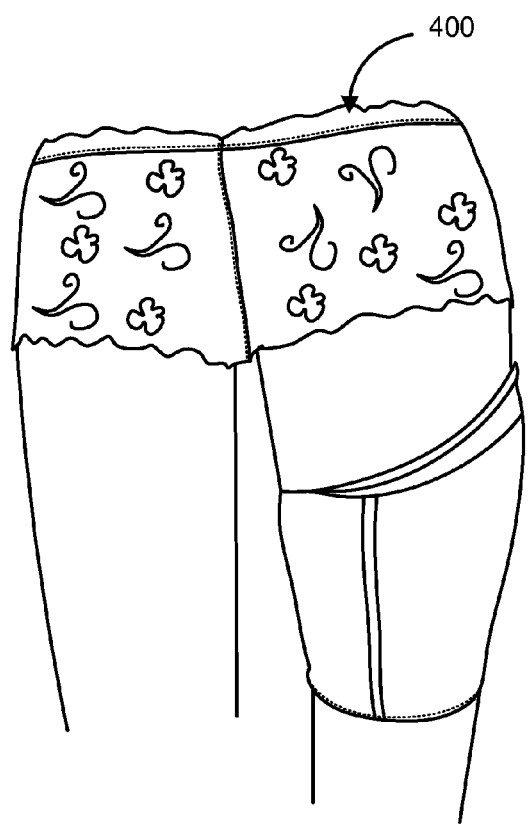

The following detailed description is of the best currently contemplated modes of carrying out the invention. The description is not to be taken in a limiting sense, but is made merely for the purpose of illustrating the general principles of the invention, since the scope of the invention is best defined by the appended claims.

FIGS. 1-10 depict urinary bag systems according to the present invention. As shown, a substantially tubular leg portion (102) is provided which may be made of a swimwear lining material (which, according to a preferred embodiment, is ninety percent (90%) polyester and ten percent (10%) spandex). There may be a substantially rectangular urine bag pouch (110) affixed to the substantially tubular leg portion (102), the substantially rectangular urine bag pouch (110) having a top side (116), left side (118), right side (120), bottom side (122), outside side portion (124) and inside side portion (126), and having a substantially rectangular cutout opening (106) along the outside side portion (124) and corresponding inside side portion (126) of the substantially rectangular urine bag pouch (110), a valve opening (112) along at least a portion of the bottom side (122) and a top opening (128) along the top side (116). According to one embodiment, at least a portion of one of the left side (118), right side (120), bottom side (122) is attached to the substantially tubular leg portion (102) by a gusset. The gusset may be an elastic gusset. A gusset is typically a triangular insert, sewn in the seam of a garment, for added strength or expansion. An elastic gusset uses a triangular insert made of an elastic material, such as 1 inch white bad knit nylon and lycra elastic. There is also at least one support opening (130) along the top (132) of the substantially tubular leg portion (102). As shown, the support opening (130) may be a eyelet, grommet or a reinforced button hole. There is also a support garment. The support garment may be underwear (200), brief (300), belt (400) and tubular fabric panel. The terms belt (400) and tubular fabric panel are interchangeable and depicted throughout. The belt (400) according to the present invention may be a tubular fabric panel. According to a preferred embodiment, it should be a tubular piece of fabric designed to be worn around the waist of the wearer and should be at least 2 inches to 10 inches in width, preferably around 4-6 inches in width. The width (402) is the measurement depicted in FIG. 6D. This provides support and comfort. The belt, according to one embodiment, is swimwear lining material, ninety percent (90%) polyester and ten percent (10%) spandex. According to another embodiment, the belt is lace, which is ninety three percent (93%) nylon and seven percent (7%) spandex lace. The support garment may be a brief, made of, for example, 100% Algodo'n/Cotton.

Figure 6A:
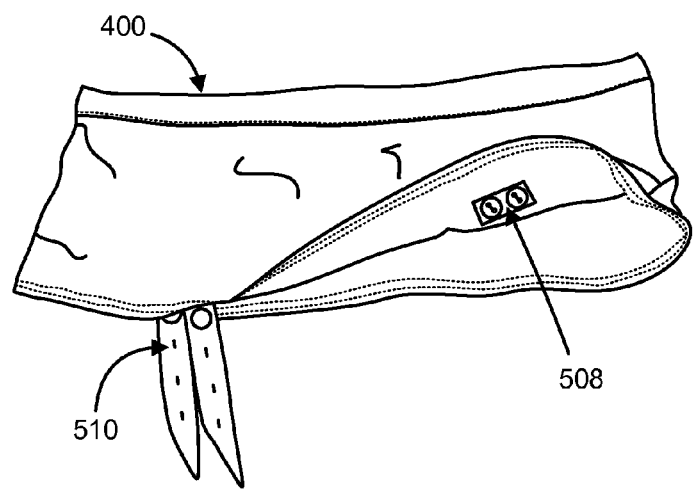
FIGS. 6A-6E depict a urine bag holder system, according to aspects of the present invention.
Figure 6B:
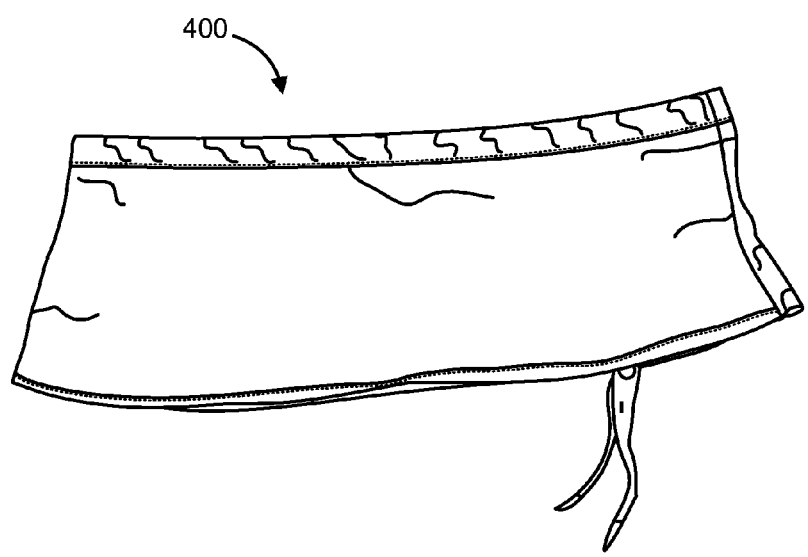
Figure 6C:
Figure 6D:
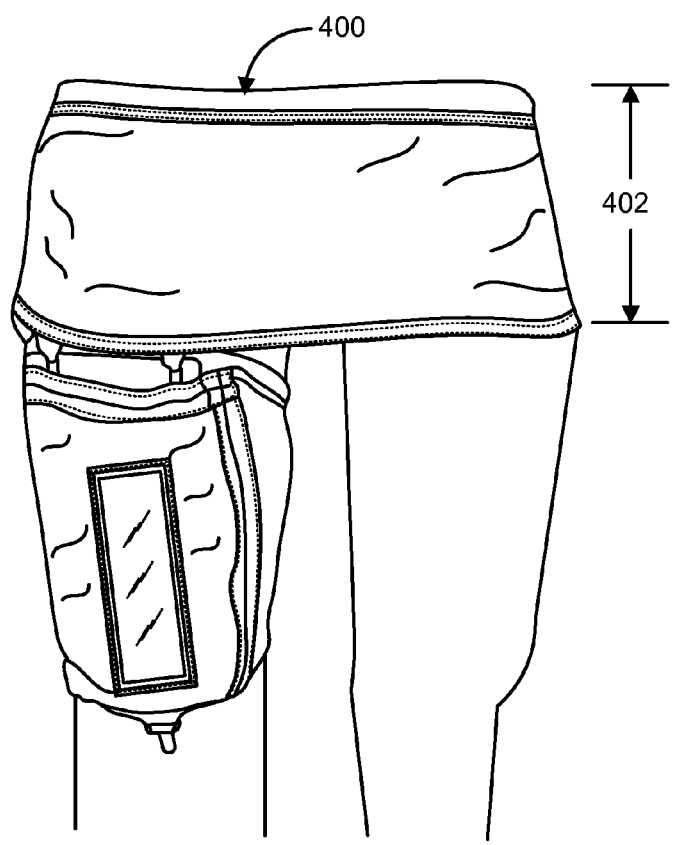
Figure 6E:
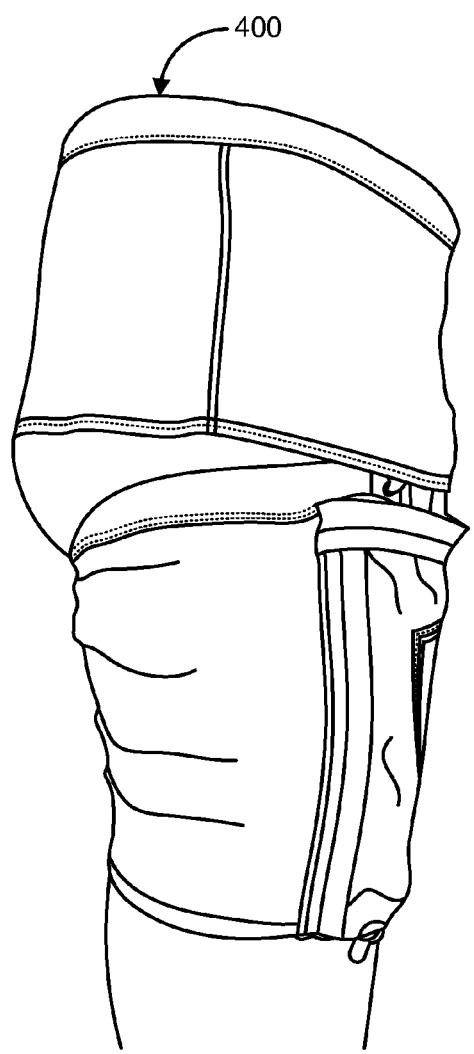
Figure 7A:
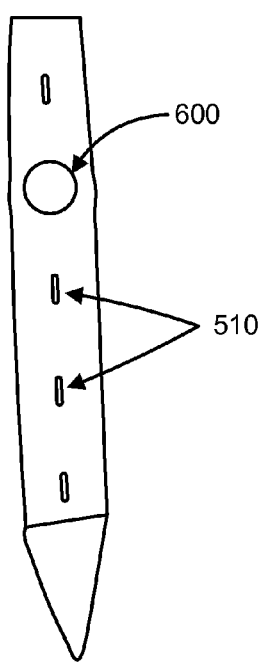
FIGS. 7A-7B depict an attachment device, according to aspects of the present invention.
Figure 7B:
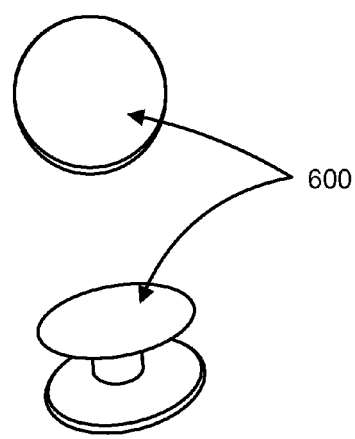
Figure 8:
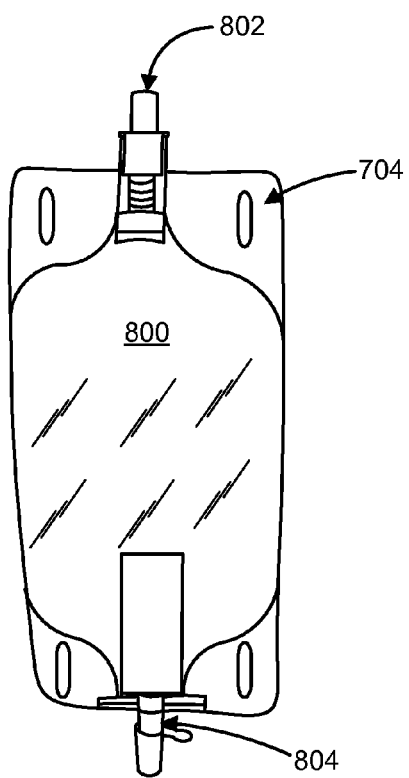
FIG. 8 depicts a urine bag, as may be used in the present invention.
Figure 9:
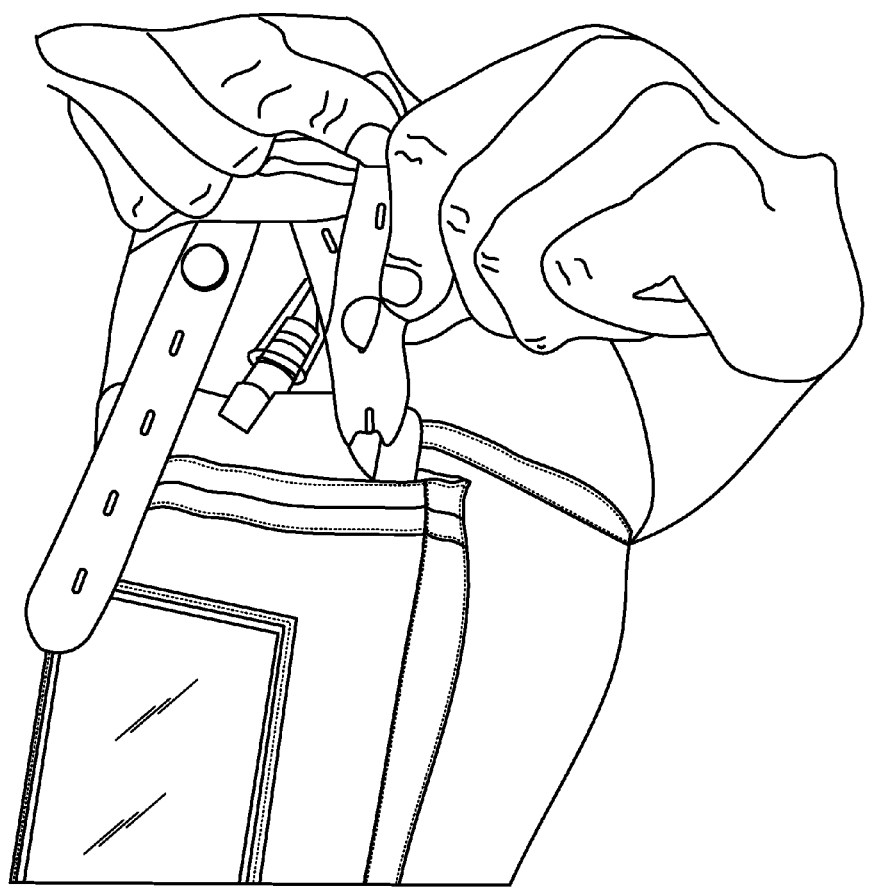
FIG. 9 depicts a urine bag holder system, according to aspects of the present invention.
Figure 10:
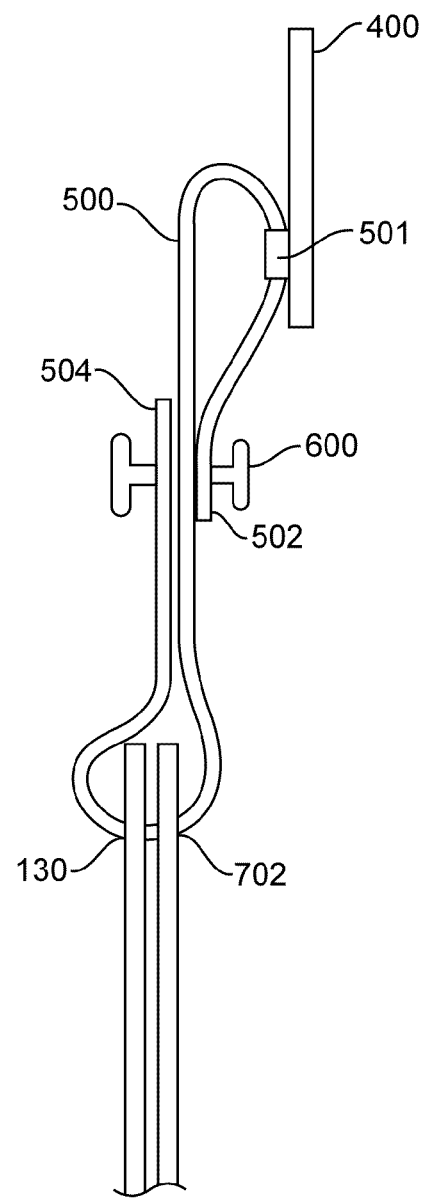
FIG. 10 depicts a urine bag holder system, according to aspects of the present invention.

There may also be at least one strap (500) having at least one attachment device (506), a first end (502) and a second end (504), the first end (502) removably attached to the support garment (e.g. 200, 300, 400) by the at least one attachment device (506) and the second end (504) removably attached to the at least one support opening (130) along a top portion (132) of the substantially tubular leg portion (102) by the at least one attachment device (506). The strap may be a garter, such as standard latex-free bag straps with plastic with double sided buttons. FIG. 6A depicts one embodiment of the present invention. As shown, there is a belt (400), having a two buttons (508) sewn into the inside of the belt (400) on top of a fabric strap (509). Note, that the inside of the right side is shown, but the left side has identical buttons (508) sewn into the inside of the belt and the strap (500) is attached to the left side buttons and hanging down. The strap (500) has a series of button holes (510). A first end (502) of the strap (500) is attached by the button hole (510) and the button (508) sewn into the inside. The button (508) and the button hole (510) make up the attachment device. A double button (600) may be attached to the second end (504) of the strap (500). The second end (504) of the strap may be threaded through the support opening (130), then through a urine leg bag top cut out (702), then be folded back up closed by attaching the button hole (510) to the double button (600). FIGS. 9 and 10 depict a single double button (600). In which the first end (502) of the strap (500) is threaded through an attachment device which is a piece of fabric (501) sewn into the inside of the belt (400), then wrapped back down and a button hole (510) in the strap (500) closed on double button (600). The second end (504) of the strap (500) is threaded through a urine leg bag top cut out (702), then the support opening (130) then folded back up and a second button hole along the second end (504) of the strap is attached to the other side of the double button (600). FIG. 10 depicts a cut away side view of FIG. 9, to provide additional detail. The attachment device may be selected from the group consisting of hook and loop fastener, a button and at least one button hole, fabric strap, snap fasteners, buckles, clips.

According to one embodiment, as shown in FIGS. 1A, 1D, 2D, 3D, 4D, 5C, 5D, 5E, 6C and 6E, the substantially tubular leg portion is wider at a top portion than a bottom portion and tapering from the top portion to the bottom portion.

There may also be a transparent water resistant layer (106) fixedly attached to the inside side portion (126) of the substantially rectangular urine bag pouch (110) and at least slightly larger than the substantially rectangular cutout opening (121). This is to say that the transparent water resistant layer (106) may just cover the substantially rectangular cutout opening (121). Also, the transparent water resister layer (106) may provide a water resistant liner, lining the pocket formed by the substantially tubular leg portion and the substantially rectangular urine bag pouch affixed thereto. In this way, it would provide additional leakage protection against the leg of the wearer.

There may also be a standard urine leg bag (800), such as a Bard® urine leg bag, having first top cut out (702), second top cut out (704), a top valve (802) and a drainage valve (804), wherein the at least one attachment device is a first attachment device having a first end and a second end and a second attachment device having a first end and a second end, the second end of the first attachment device removably attached to the first top cut out (702), the second end of the second attachment device removably attached to said second top cut out (704), and the standard urine leg bag (800) is placed inside the top opening (128) of the substantially rectangular urine bag pouch (110) and the drainage valve (804) protrudes through the valve opening (112). The urine bag is generally flat when empty and formed of flexible thermoplastic sheet material. When in use, the bag fills with urine into the top valve (802) and the outer wall of the bag expands to accommodate the fluid. If there are gussets, for example elastic gussets, along the left side (118) and right side (120), the substantially rectangular urine bag pouch (110) would expand and contract according to the amount of urine in the urine bag (800). In this way, buckling is avoided and contact with the wearers skin is minimized.

The term "attachment devices" describes what are commonly referred to in the art as fastener components, where the first and second ends are complementary and connect together. Examples of attachment devices, without limitation, may be a hook and loop fastener, a button and a button hole, snap fasteners, buckles, clips.

Aspects of the present invention provide systems and methods for securing a patient's urinary drainage bag. This device is designed to enhance the quality of life of a patient who requires a urinary drainage bag (such as that required by nephrostomy tubes or catheters) enabling them to experience security, increased mobility and comfort. The invention may consist of (1) urine leg bag sleeve (2) male and female gartered brief underwear and (3) female and unisex garter belt. The urine leg bag sleeve has a window pouch which holds and supports a urine leg bag. The sleeve may have has eyelets at the top thigh area of the sleeve wherein garters are fed through eyelets and standard urine leg bag top cut outs to secure the sleeve and the urine leg bag to the brief or belt. The brief has adjustable garters attached to the underside of the front thigh legs. The belt has adjustable garters attached to the underside of the front thigh area. The brief and belt are worn exclusively with the sleeve. The "top hold" garters are one reason the user's urine leg bag remains secure and comfortable, enhancing the patient's mobility with no concern of slippage of their urine leg bag throughout their daily activities. The unique "window" pouch allows the patient to easily view the quantity and quality of their urine in the leg bag. With window viewing of the urine leg bag, a patient can easily view blood in urine or the possible malfunction of their nephrostomy tube by the lack of urine found in their bag without having to remove their urine bag from the sleeve. According to one aspect of the present invention, the apparatus may be utilized as follows: User steps into the support garment brief or belt and pulls up to the waist. (Brief or Belt should fit snugly but not tight.) Garter straps are attached to the front of the Brief or Belt and hang; User then inserts the urine leg bag into the window pouch (substantially rectangular urine bag pouch) so that urine drainage valve is exposed through an opening at the bottom of the pouch for the valve, to allow for easy emptying. The user pulls the substantially tubular leg portion (sleeve) with urine leg bag in the pouch up high on the thigh, as close to the groin area as possible. (Sleeve should feel comfortable or snug. Not tight.) The user takes the pointed end of each garter strap and pulls one strap through each top eyelet on the sleeve at the same time also feeding it through the top cut outs of the urine leg bag that is inside the pouch (eyelets and urine bag cutouts may line up for easy garter strap feeding). Once garter straps are fed through both openings, garter is fastened by buttoning the straps onto a double sided button located on the garter strap. This provides a unique and superior urine bag system for many reasons including the urine leg bag is housed in window pouch sleeve that is comfortable, the urine leg bag sleeve allows user to monitor urine color and quantity, the urine leg bag is secured with top hold garters to a brief or belt, the urine leg bag resists slippage or fall down the user's leg, the urine leg bag sleeve, brief and belt are comfortable, the urine leg bag sleeve, brief and belt is easy to wear, the urine leg bag sleeve has a window pouch. Systems and methods of the present invention, thus, help increase the comfort, ease of use and quality of life of individuals that require a urinary drainage bag.

The present invention has been described in relation to particular examples, which are intended to be illustrative rather than restrictive, with the scope and spirit of the invention being indicated by the following claims and their equivalents. It should be understood that the foregoing relates to preferred embodiments of the invention and that modifications may be made without departing from the spirit and scope of the invention as set forth in the following claims.

The invention claimed is:

1. A urinary bag system comprising:
   A substantially tubular leg portion having two support openings along a top portion;
   a substantially rectangular urine bag pouch affixed to said substantially tubular leg portion, said substantially rectangular urine bag pouch having a top side, left side, right side, bottom side, outside side portion and inside side portion, and having a substantially rectangular cutout opening along said outside side portion and corresponding said inside side portion of said substantially rectangular urine bag pouch, a valve opening along at least a portion of said bottom side and a top opening along said top side;
   a urine leg bag having two top cut outs, wherein said urine leg bag sits inside said substantially rectangular urine bag pouch;
   a support garment;
   two straps each having at least one attachment device, a first end and a second end, said first end removably attached to said support garment by said at least one attachment device and said second end removably attached to said at least one support opening along a top portion of said substantially tubular leg portion and one top cut out of the urine leg bag by said at least one attachment device, wherein the first end of each of the two straps is threaded through a piece of fabric sewn into the inside of the support garment, then wrapped back down and a button hole in the strap closed on a double button, the second end of the strap is threaded through one urine leg bag top cut out and the support opening then folded back up and a second button hole along the second end of the strap is attached to the other side of the double button.

2. A urinary bag system of claim 1, said substantially tubular leg portion being wider at a top portion than a bottom portion and tapering from said top portion to said bottom portion.

3. A urinary bag system of claim 1, further comprising a transparent water resistant layer fixedly attached to said inside side portion of said substantially rectangular urine bag pouch and at least slightly larger than said substantially rectangular cutout opening.

4. The urinary bag system of claim 1, wherein said support garment is selected from the group consisting of underwear, brief, belt and tubular fabric panel.

5. The urinary bag system of claim 1, further comprising a standard urine leg bag having first top cut out, second top cut out, a top valve and a drainage valve, wherein said at least one attachment device is a first attachment device having a first end and a second end and a second attachment device having a first end and a second end, said second end of said first attachment device removably attached to said first top cut out, said second end of said second attachment device removably attached to said second top cut out, and said standard urine leg bag is placed inside said top opening of said substantially rectangular urine bag pouch and said drainage valve protrudes through said valve opening.

6. The urinary bag system of claim 1, wherein said attachment device is selected from the group consisting of hook and loop fastener, at least one button and at least one button hole, at least one double button and at least one button hole, snap fasteners, buckles, clips.

7. The urinary bag system of claim 1, further comprising a gusset between at least a portion of at least one of said left side, said right side, said bottom side and said substantially tubular leg portion.

8. The urinary bag system of claim 7, wherein said gusset is an elastic gusset.

9. The urinary bag system of claim 1, wherein said support opening is selected from the group consisting of eyelet, grommet and reinforced button hole.

10. A urinary bag system comprising:
    A substantially tubular leg portion having two support openings along a top portion;
    a substantially rectangular urine bag pouch affixed to said substantially tubular leg portion, said substantially rectangular urine bag pouch having a top side, left side, right side, bottom side, outside side portion and inside side portion, and having a substantially rectangular cutout opening along said outside side portion and corresponding said inside side portion of said substantially rectangular urine bag pouch, a valve opening along at least a portion of said bottom side and a top opening along said top side;
    a gusset between at least a portion of at least one of said left side, said right side, said bottom side and said substantially tubular leg portion;
    a urine leg bag having two top cut outs, wherein said urine leg bag sits inside said substantially rectangular urine bag pouch;
    a support garment;

at least one strap having at least one attachment device, a first end and a second end, said first end removably attached to said support garment by said at least one attachment device and said second end removably attached to said at least one support opening along a top portion of said substantially tubular leg portion and one top cut out of the urine leg bag by said at least one attachment device, wherein the first end of each of the two straps is threaded through a piece of fabric sewn into the inside of the support garment, then wrapped back down and a button hole in the strap closed on a double button, the second end of the strap is threaded through one urine leg bag top cut out and the support opening then folded back up and a second button hole along the second end of the strap is attached to the other side of the double button.

11. A urinary bag system of claim 10, said substantially tubular leg portion being wider at a top portion than a bottom portion and tapering from said top portion to said bottom portion.

12. A urinary bag system of claim 10, further comprising a transparent water resistant layer fixedly attached to said inside side portion of said substantially rectangular urine bag pouch and at least slightly larger than said substantially rectangular cutout opening.

13. The urinary bag system of claim 10, wherein said support garment is selected from the group consisting of underwear, brief, belt and tubular fabric panel.

14. The urinary bag system of claim 10, further comprising a standard urine leg bag having first top cut out, second top cut out, a top valve and a drainage valve, wherein said at least one attachment device is a first attachment device having a first end and a second end and a second attachment device having a first end and a second end, said second end of said first attachment device removably attached to said first top cut out, said second end of said second attachment device removably attached to said second top cut out, and said standard urine leg bag is placed inside said top opening of said substantially rectangular urine bag pouch and said drainage valve protrudes through said valve opening.

15. The urinary bag system of claim 10, wherein said attachment device is selected from the group consisting of hook and loop fastener, at least one button and at least one button hole, at least one double button and at least one button hole, snap fasteners, buckles, clips.

16. The urinary bag system of claim 10, wherein said gusset is an elastic gusset.

17. The urinary bag system of claim 10, wherein said support opening is selected from the group consisting of eyelet, grommet and reinforced button hole.

* * * * *